United States Patent [19]

Singer

[11] Patent Number: 4,560,516
[45] Date of Patent: Dec. 24, 1985

[54] PROCESS FOR THE PRODUCTION OF ETHYLENEDIAMINE TETRAACETONITRILE

[75] Inventor: John J. Singer, Hollis, N.H.

[73] Assignee: Ciba-Geigy Corporation, Ardsley, N.Y.

[21] Appl. No.: 696,782

[22] Filed: Jan. 31, 1985

Related U.S. Application Data

[63] Continuation-in-part of Ser. No. 526,230, Aug. 24, 1983, abandoned, which is a continuation of Ser. No. 333,138, Dec. 21, 1981, abandoned.

[51] Int. Cl.$^4$ .................... C07C 120/00; C07C 121/43
[52] U.S. Cl. ...................... 260/465.5 A; 260/465.5 R
[58] Field of Search ................................ 260/465.5 A

[56] References Cited

U.S. PATENT DOCUMENTS

| | | | |
|---|---|---|---|
| 2,130,505 | 9/1938 | Munz | 562/566 |
| 2,164,781 | 7/1939 | Platz et al. | 562/575 |
| 2,205,995 | 6/1940 | Ulrich et al. | 260/465.5 A |
| 2,384,813 | 9/1945 | Coleman | 423/316 |
| 2,407,645 | 9/1946 | Bersworth | 260/699 X |
| 2,855,428 | 10/1958 | Singer et al. | 260/465.5 A |
| 3,061,628 | 10/1962 | Singer, Jr. et al. | 260/465.5 A |
| 3,424,783 | 1/1969 | Harper et al. | 260/465.5 A |
| 3,463,805 | 8/1969 | Morgan et al. | 260/465.5 A |
| 3,515,742 | 6/1970 | Morgan et al. | 260/465.5 A |
| 3,644,444 | 2/1972 | Popper et al. | 562/566 X |
| 3,679,729 | 7/1972 | Daniels | 260/465.5 A |
| 3,714,223 | 1/1973 | Godfrey et al. | 260/465.5 A |
| 3,758,534 | 9/1973 | Popper et al. | 562/566 X |
| 3,907,858 | 9/1975 | Davis et al. | 260/465.5 A |
| 3,925,448 | 12/1975 | Lanier | 260/465.5 A |
| 3,959,342 | 5/1976 | Homberg et al. | 562/572 X |
| 3,988,360 | 10/1976 | Gaudette et al. | 260/465.5 A |

FOREIGN PATENT DOCUMENTS

| | | | |
|---|---|---|---|
| 1418538 | 10/1968 | Fed. Rep. of Germany | 260/465.5 A |
| 49-126620 | 12/1974 | Japan | 260/465.5 A |

OTHER PUBLICATIONS

Walker, "Formaldehyde", 3rd. Ed., 1975, Krieger Pub. Co., Huntington, N.Y., pp. 511–551.

*Primary Examiner*—Joseph Paul Brust
*Attorney, Agent, or Firm*—Edward M. Roberts; Bruce M. Collins

[57] ABSTRACT

Ethylenediamine tetraacetonitrile is prepared in a two stage process by cyanomethylating an ethylenediamine formaldehyde adduct with hydrocyanic acid at 30° C. or less under basic conditions (pH 8 to 10) to form, in a first discrete stage, ethylenediamine diacetonitrile (ED-DiN) which is soluble in the reaction mixture. The solution of EDDiN is then further cyanomethylated under acidic conditions with formaldehyde and hydrocyanic acid in slight excess to form ethylenediamine tetraacetonitrile (EDTN). The precipitated EDTN, with or without isolation, can be hydrolyzed to form ethylenediamine tetraacetic acid in a stock solution for further processing. The process reduces the need for toxic cyanide waste treatment and greatly simplifies the procedures needed to protect the environment.

7 Claims, No Drawings

PROCESS FOR THE PRODUCTION OF ETHYLENEDIAMINE TETRAACETONITRILE

CROSS REFERENCE

This is a continuation-in-part of Ser. No. 526,230 filed Aug. 24, 1983, now abandoned, which in turn is a continuation of Ser. No. 333,138 filed Dec. 21, 1981, now abandoned.

BACKGROUND OF THE INVENTION

Various processes for the preparation of aminoacid chelating and metal ion sequestering agents are known including the coupling of an amine with chloracetic acid (U.S. Pat. No. 2,130,505) and the oxidation of ethanol amines (U.S. Pat. No. 2,384,816).

A more commonly used method utilizes hydrolysis of the appropriate nitrile, (U.S. Pat. No. 2,407,645) including variation such as separate formation, separation and hydrolysis of the nitrile (U.S. Pat. Nos. 2,164,781 and 2,205,995). In U.S. Pat. No. 2,855,428, ethylenediamine tetraacetonitrile (EDTN) is synthesized by introducing ethylenediamine amine to an acidic medium of formaldehyde and hydrocyanic acid. The nitrile is directly precipitated in the acidic medium as formed and recovered in good yields but requires a glass-lined (or other acid-resistant) reactor, good agitation and highly efficient heat transfer equipment since the reaction is highly exothermic and HCN will vaporize in the absence of high capacity cooling equipment. Reaction times are determined by the rate at which heat can be removed from the reaction medium. The process nevertheless has been practiced and continues to be practiced on a large scale ever since its initial commercial use.

U.S. Pat. No. 3,424,783 describes a variant wherein the cyanomethylation is conducted in acidic media. U.S. Pat. Nos. 3,644,444, 3,758,534, 3,679,729 and 3,714,223 disclose various specific acid pH ranges and temperature ranges, but in each case the tetracetonitrile is isolated and washed before saponificature as a prerequisite to pure EDTA acid preparation, requiring sophisticated equipment and extensive waste treatment operations. Failure to treat the reaction product as described therein results in lower yields.

U.S. Pat. Nos. 3,959,342 and 2,855,428 disclose formation of nitrilotriacetonitrile (NTN) and hydrolysis to the corresponding acid (NTA). Cyanomethylation (leading to NTN) is performed under acid conditions and provides yields of NTN in the range of 80 to about 95 wt % (based on ammonia or hexamethylenetetramine).

These older techniques involve close control of the exothermic reactions and moreover require "HCN rated" auxillary equipment. Not only is this more expensive, it precludes the use of more efficient heat exchange equipment. Moreover, the process can pose environmental hazards as a result of the HCN used and the by-products normally produced.

DETAILED DESCRIPTION

Ethylenediamine tetraacetonitrile is prepared in high quality and almost quantitative yield by first forming an adduct from an admixture of two moles of formaldehyde (HCHO) with one mole of ethylenediamine [(NH$_2$CH$_2$)$_2$]. This adduct then is subject to a first cyanomethylation stage by the addition of two moles of hydrocyanic acid (HCN) at a strongly alkaline pH of about 8 to about 10 and at a temperature at or below about 30° C. to form ethylenediamine diacetonitrile (EDDiN), [(CNCH$_2$NHCH$_2$—)$_2$]. The EDDiN is soluble and remains dissolved in the reaction mixture. The degree of substitution is pH dependent and not a function of concentration of reactants.

The solution of EDDiN next is subjected to a second stage cyanomethylation by introducting it into an acid mixture containing two moles each of HCN and HCHO at a pH of at or below 1, preferably about 0.5. A slight excess of HCN (10 mole %) is preferred to assure high yields. The pH during the introduction of the EDDiN is preferably maintained at or below about 1.0 by the addition of acid and control of the rate of EDDiN addition. The exotherm of this second stage cyanomethylation is controlled adiabatically by addition of coolant, either pre-cooled mother liquor from a previous reaction or an inert liquid such as water so that the temperature stays below about 70° C. during the reaction. The heat released in the reaction is absorbed in the sensible heat rise of the reaction medium or mass to 70° C. No directly applied external cooling need be used. The solution of dinitrile can be added very rapidly since the heat exchange capacity no longer limits the speed at which the reaction can be carried to completion.

These reactions may be summarized as follows:

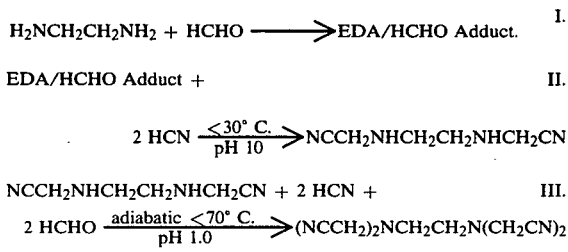

$$H_2NCH_2CH_2NH_2 + HCHO \longrightarrow EDA/HCHO \text{ Adduct.} \quad I.$$

EDA/HCHO Adduct + II.

$$2 \text{ HCN} \xrightarrow[\text{pH 10}]{\leq 30° \text{ C.}} NCCH_2NHCH_2CH_2NHCH_2CN$$

NCCH$_2$NHCH$_2$CH$_2$NHCH$_2$CN + 2 HCN + III.

$$2 \text{ HCHO} \xrightarrow[\text{pH 1.0}]{\text{adiabatic } <70° \text{ C.}} (NCCH_2)_2NCH_2CH_2N(CH_2CN)_2$$

In order to maintain the first stage cyanomethylation below 30° C., it is advantageous to utilize an adduct solution cooled to or below 30° C. This reduces the refrigeration required to prevent color-forming side reactions and lower yields which are observed at temperatures above about 30° C. The cooled solution from this first stage cyanomethylation in turn is kept below about 30° C. when fed into the subsequent second stage cyanomethylation.

The second stage cyanomethylation reaction of EDDiN with HCN and HCHO is carried out in an acidic media, adding cooled (below 30° C.) 50% H$_2$SO$_4$ as necessary to maintain the pH at or below about 1.0. Owing to the precipitation of EDTN, it is difficult in prior art processes to cool the reaction mixture during the reaction without fouling of heat transfer surfaces, thereby requiring longer reaction times and producing a concurrent reduction in yields and increase in by-product. The present reaction, however, is carried out adiabatically using the sensible heat rise from below 30° C. to 70° C. by auxiliary cooling, specifically by adding a coolant, most notably recycled cooled mother liquor (after EDTN separation) to the reaction medium as required, the final temperature being below about 70° C. (to prevent side reactions) and preferably about 65° C. to ensure substantially quantitative completion of the EDTN formation. In the prior art processes, the mother liquors can not be effectively recycled due to the presence of by-products and excessive color, thus increasing the amount of toxic waste.

Upon completion of the second stage cyanomethylation, the EDTN forms rapidly as large crystals and may be separated from the mother liquor, washed, preferably with water, and then hydrolyzed. Hydrolysis to EDTA can be effected in conventional caustic medium to produce very pure EDTA as the tetrasodium salt in solution. This is a stock solution for the formation of further EDTA products such as the acid and other salts.

Alternatively, the nitrile may be saponified without separation from all or part of the mother liquor or reaction liquor and then (if necessary to remove residual HCN) after treatment with formaldehyde, precipitated with acid at pH 3 or lower to form EDTA free acid in essentially quantitative yield of high purity. The ammonia liberated by the hydrolysis of the nitrile groups can be recovered, preferably in anhydrous form, as a useful by-product. Any excess filtrate from the EDTN formation and separation containing excess HCHO and HCN can be treated, optionally in the saponification of EDTA, to produce a non-toxic material which can be easily disposed of, without the need for the usual separate treatment and disposal of toxic waste.

The overall process leading to EDTN can be carried out on a batch, semi-batch or continuous basis. The best yields and quality have been obtained in the preferred semi-batch procedure as follows.

To facilitate heat removal, the initial adduct formation is preferably separated from the first stage cyanomethylation. The reaction of two moles of HCHO with the EDA to form the adduct liberates twice the amount of heat as does the subsequent formation of the dinitrile: ($-31.1$ Kcal vs. $-15.1$ Kcal). Any concentional cooling system of sufficient capacity, such as heat exchangers or cooling coils in holding tanks in which the aqueous solution of HCHO (37–50% HCHO) is reacted with the EDA in 2:1 molar proportion, can be used to remove this significant quantity of heat.

Feed rates of the two components and cooling rates are adjusted in response to thermometric sensors. Preferably the final adduct temperature should be about 20°–25° C. and care should be taken not to exceed 30° C. during formation of the EDA/HCHO adduct. The pH of the adduct solution is about 9–10.

The first stage cyanomethylation is performed by allowing the EDA/HCHO adduct in aqueous solution to react with a stoichiometric quantity (2 molar equivalents) of HCN at a highly alkaline pH of 8 to 10. This step of the reaction is most thermosensitive and is conducted below 30° C. by feeding 100% HCN slowly below the surface of the adduct solution in a well agitated and cooled reaction vessel. The exothermic reaction of the HCN with the adduct is moderately rapid. The reaction is substantially quantitative (99+%) within about 30 minutes after completion of the HCN addition. The formation of the dinitrile, rather than the tetranitrile, is pH dependent. The reaction product, EDDiN, remains in solution, thus greatly facilitating cooling, and this solution is maintained at about 20°–25° C. for transferral to the next step.

EDTN is prepared by adding, at a controlled rate, the EDDiN solution to a mixture of $H_2SO_4$, HCHO, HCN and recycled mother liquor (as coolant). Sufficient $H_2SO_4$ is desirable to maintain the pH at or below about 1.0. Excessively rapid addition of the EDDiN solution can cause the pH to rise with the promotion of the formation of side products and consequent reduction in yield. The pH of the reaction mass can be monitored by pH sensors and the rate of EDDiN addition controlled and adjusted to maintain the pH at or below about 1.0, a definite effect of addition rate vs. pH being observed. The reaction, however, can be taken to completion much faster than in the case of conventional one step EDTA production.

An excess of HCN and HCHO promotes the second stage cyanomethylation as can be seen from the following, an almost quantitative conversion to EDTN being obtained at about 10% combined molar excess:

| HCH/HCHO:EDDiN | % Molar Excess | EDTN Yield (% Theory) |
| --- | --- | --- |
| 1.8/1.8:1 | (−5%) | 85.2 |
| 2.0/2.0:1 | 0% | 94.2 |
| 2.2/2.2:1 | 5% | 96 |
| 2.4/2.4:1 | 10% | 97.99 |

The second stage cyanomethylation is exothermic ($-49$ Kcal/mole using a 50% solution of HCHO) but in contrast to the formation of EDDiN, the quality and yield of EDTN are not adversely affected if reaction temperatures are maintained below about 70° C. (color undesirably develops above about 70° C.). The product of the second stage cyanomethylation, EDTN, thus is more thermostable than that of the first stage cyanomethylation and the reaction can proceed with minimal undesired side reactions if temperatures are kept below about 70° C., preferably at about 60°–65° C. This is advantageous since the formation of solid EDTN complicated cooling whereas the soluble EDDiN can be easily cooled. Substantial completion of the reaction occurs at these temperatures within a reasonable time, e.g. one hour after completion of EDDiN addition. The reaction is best carried out adiabatically without the need for of heat exchange, surfaces of which can be fouled by formation of coatings of solids thereon.

To further assist in control of the temperature within these ranges, the initial reaction mass can be cooled by using a cooled inert liquid as a "heat sink". In the initial start up, this can be water but once on stream the liquid preferably is mother liquor from previous batches. Mother or reactant liquor from the subsequent separation step of EDTN thus is cooled to 20°–30° C. and then introduced into the reaction mass of the second cyanomethylation. Generally the amount of coolant required will be such as to maintain a slurry concentration in the reaction mass of 15 to 30%, preferably in the range 17 to 23% EDTN solids. The addition can be controlled by temperature sensors in the reaction mass. A further advantage for using the recycled mother liquor for diluting and cooling the reaction mass is that excess HCN/HCHO used in this stage is re-utilized, thus maximizing the overall use of these materials, reducing aftertreatments, and minimizing the amounts of these materials which are lost when excess reaction medium from EDTN is saponified.

Approximately 60–70% of the reaction liquor can be recycled. A suitable treatment of the HCN/HCHO excesses before disposal of mother liquor which is not recycled or which is not added to the saponification reaction is to render the material strongly alkaline and then to heat to about 80°–100° C. The cyanide is decomposed to less than 10 ppm and the resulting ammonia is recovered.

The final EDTN reaction mass need not be cooled before the slurry is allowed to settle and a portion of the mother liquor removed for recycling. Any mother liquor removed, however, must be cooled before recycling since it is a "heat sink" for the next reaction to be run. Cooling is simplified since the liquid contains only small amounts of nitrile as suspended particles and conventional heat exchangers may be used with minimal fouling.

The hot concentrated slurry thus is adjusted to approximately 30% solids by the addition of cold water. After mixing for a few minutes the slurry is transferred to a holding tank containing enough caustic to produce a pH of 9.0 or higher for the slurry when neutralization of the acids (HCN, $H_2SO_4$) is complete.

If pure solutions of EDTA sodium salt are desired, the nitrile may be isolated (after neutralization) using conventional centrifuges or filtering equipment. Ordinary ventilation equipment is adequate for worker safety. After isolation, the nitrile may be reslurried with water and saponified in the conventional manner, the mother liquor and wash water being temporarily stored in holding tanks. If EDTA as the free acid is to be prepared, the neutralized EDTN slurry (about 30%) in water is pumped directly to the saponification tank along with any alkaline mother liquor and wash water from previous runs in which the nitrile was isolated and washed. Following saponification, acidification (to pH 3) precipitates pure EDTA which can be isolated and dried with conventional equipment.

The process can also be performed on a continuous basis. A previously formed and cooled EDA/HCHO adduct (1:2 moles) thus is fed into a continuously stirred vessel where it is allowed to react with a stream of HCN. The yields of EDDiN from this continuous first stage cyanomethylation (as determined by a batch-wise second stage cyanomethylation to EDTN) are essentially quantitative based on ethylene diamine. The reactor temperature is kept below 30° C. and the residence time in the reactor is about 30 minutes. Variations in HCN concentration in the vessel indicate that in a continuous reactor, an initial excess of HCN does not ensure fuller completion of the reaction within the stated residence-time parameter and will not be available in the second stage cyanomethylation whereas a deficiency of HCN will affect the second reaction by increasing pH, lowering HCN concentrations and making adjustment necessary.

EDDiN reacted in a continuous reactor train with additional HCN/HCHO in an acid medium shows yields of 75 to 96% of theoretical (based upon 100% EDDiN feed) depending upon dwell time and HCN/HCHO feeds. Higher yields are obtained with HCN/HCHO excesses ranging around 30 mole % and at dwell times of from one to two hours. However, incremental yields, determined at fixed periods during extended runs (2½ to 9 hours), are progressively lower at succeeding intervals (after establishing the reaction equilibrium), indicating accumulation of solid EDTN in the reactor train. It is because of such solid accumulation in the continuous processing schedule that the semi-batch process is preferred.

Typical embodiments for practicing the process of this invention are set forth in the following examples. These show both the preferred and alternate modes. It is to be understood that while typical apparatus is described in some of the examples, equivalent apparatus suitable for performing the described unit operations may be substituted.

EXAMPLE 1

Semi-Batch Procedure

To a 500 ml reactor flask equipped with a mechanical stirrer, Friedrichs condenser chilled with ice water, thermometer, 250 ml dropping funnel with dip tube, and an ice bath, charge 120.0 g of aqueous 50% formaldehyde (HCHO). Charge to the dropping funnel 120.0 g of 100% ethylenediamine (EDA). Begin adding the EDA dropwise into the reactor at a rate such that the temperature is maintained below 30° C. with the ice bath.

After the addition is complete, slowly charge 54.0 g of 100% HCN through the dropping funnel with its dip tube maintained below the surface of the liquid adduct, so that the temperature is continuously maintained below 30° C. (with ice bath). After the HCN addition is complete, stir for about 30 minutes. The EDDiN formed in solution is then ready for the second stage cyanomethylation.

To a 2-liter reactor flask, equipped with a mechanical stirrer, Friedrichs condenser chilled with ice water, thermometer, 250 ml dropping funnel, and pH probe, charge 713 g of distilled water, 54.8 g of 96% sulfuric acid, and 140.0 g of formaldehyde. Cool the reactor contents to 20° C. with an ice bath and charge 64.8 g of 100% HCN, charge the EDDiN solution to the contents of the flask while following the pH of the reaction mass. Control and adjust the rate of addition so that the pH is maintained between 0.5 and 1.0 during the course of the addition. The reaction is carried out adiabatically. The temperature will rise from about 25°–30° C. to 60°–65° C. and is maintained at this upper level for from about one half to one hour after complete addition of EDDiN and before isolation of the precipitated EDTN. Temperature is controlled by addition of cooled reaction liquor from a previous run or with cooled water.

Cool the resulting slurry to 30° C., filtered, and wash the wet cake with distilled water. Dry the wet cake under vacuum at 50° C. or in a hot air oven at 100° C.

Slurry the separated EDTN solid with sufficient 25%–33% NaOH to give a mole ratio of 1.0/4.4 EDTA to NaOH. Pump the slurry from the slurry vessel to a second vessel containing a heel of hot (100°–104° C.) sodium EDTA solution (38%).

After the addition is complete, the reaction mass is boiled gently until no ammonia can be detected at the vent. The solution is then treated for trace cyanide by addition of formaldehyde. Add water to dilute the solution to 30% EDTA acid content. Yield 98% of theory.

EXAMPLE 2

The continuous preparation of EDTN is performed in two phases. The first phase consists of the first stage cyanomethylation reaction wherein the adduct of EDA/HCHO is cyanomethylated in a continously stirred reactor and the solution of reaction product (EDDiN) is then further cyanomethylated in the second stage to EDTN in a continuous stirred reactor with an acid mixture of HCHO and HCN in 10% excess over stoichiometric.

Charge one mole of EDDiN solution (prepared in the semi-batch procedure of Example 1) in portions, as needed, to a jacketed reservoir, cooled with ice water, leading via a metering pump to the first stage of a cascaded series of insulated one-liter CSTR vessels equipped with a side-arm overflow pipe to the next vessel.

Charge as needed mixture of 713 g of $H_2O$, 54.8 g of $H_2SO_4$ (96%), 144 g of 50% aqueous HCHO and 64.8 g of 100% HCN to a reservoir, fitted with an ice water-cooled Friedrichs condenser, and connected via an adjustable metering pump to the same CSTR cascade.

Pump the EDDiN solution and the acidic HCHO/HCN mixture to the first-stage of the cascade. Residence times stoichiometry are controlled and determined by the total pumping rate and pumping rate-ratio respectively. Control pH to at or below 1.0 as needed by addition of 50% $H_2SO_4$ and control temperature by addition of cold recycled reaction liquor. Slurry overflow from previous reactions is collected, filtered, washed and reslurried for saponification.

In the two and three stage cascades with residence times of 2 and 1 hour respectively, overall yields of 96 and 94% based on EDDiN are obtained.

EXAMPLE 3

Continuous Hydrolysis EDTN to EDTA Tetrasodium Salt

The continuous operation of the EDTN hydrolysis to form the EDTA tetrasodium salt stock solution is carried out in a manner similar to the hydrolysis step of Example 1 with the exception that the EDTN/NaOH slurry is pumped into one or more CSTR stages. The overflow of the last CSTR is collected for treatment with formaldehyde for cyanide elimination.

EXAMPLE 4

Pilot Plant

EDA/HCHO Premix

Charge HCHO (50%) 685.0 lbs (71.3 gals) to a premixer (R#1). Add EDA 342.5 lbs (45.1 gals) to the premixer over a 3.67 hour period. Reactor temperature is monitored and the feed is adjusted to maintain the temperature at about 30° C. while coolant is circulated through reactor cooling coils.

Transfer the premixer contents 1027.5 lbs (116.8 gals) of EDA/HCHO adduct to a holding tank (HT#1).

First-step Cyanomethylation (EDDiN Reaction)

Charge 179.6 lbs (32.2 gals) of HCN to a weight tank (WT#1). Charge 598.6 lbs (68.0 gals) of the EDA/HCHO adduct to a (stainless steel) reaction vessel (R#2) from holding tank (HT#1). Pump HCN from the weight tank (WT#1) to a reaction vessel (R#2) over a 1.3 hour period. The reactor temperature is monitored and the feed is adjusted to maintain temperature at 30° C. while coolant is pumped through reactor cooling coils. After completion of the HCN addition, hold the reaction mass for 0.50 hours at 30° C.

Second-step Cyanomethylation (EDTN Reaction)

Charge 1469.3 lbs (172.5 gals) of water or filtrate from the EDTN separation step to a glass-lined reaction vessel (R#3). Meter 95 lbs. (0.6 gals) of $H_2SO_4$ to the reaction vessel (R#3), and charge 211.5 lbs (22.0 gals) HCHO to the same vessel together with 95.6 lbs (17.1 gals) HCN. Adjust the pH of the reactants in the vessel to pH 1.0 or lower by additional $H_2SO_4$. The temperature is maintained at 30° C. Add 792.2 lbs EDDiN solution (from the first reaction) to the reactor (R#3) over a 1.0 hour period. The temperature is allowed to rise adiabatically to 60°–65° C. but kept below 65°–70° C. by addition of chilled reaction liquor over the course of the addition period. The pH will drop to 0.5–0.8 during the course of the addition and maintain itself at this level during the run.

Allow the 4101.1 lbs (467.6 gals) contents of the second reactor of EDTN slurry to settle in the reactor after the agitator has been turned "off".

EDTN Isolation

After the slurry has settled, withdraw 1469.3 lbs (172.5 gals) of the supernatant solution, and chill to 30° C. and set aside in a hold tank. No attempt is made to remove any EDTN crystals which may form.

Add 175 gals of chilled water to the remaining contents of the reactor, restart the agitator and pump the resulting cool slurry to a holding tank containing 192 lbs of 50% caustic soda and 200 lbs of water which is at a temperature of 20° C. After all the slurry has been added, the pH is in the range of 9.0–10.0 and the temperature is less than 50° C. At this point use one of the two following procedures:

(1) Centrifuge and wash the alkaline slurry with water until free of sulfate ion ($BaCl_2$ to wash water gives no cloud). The wet cake will contain from 5 to 10% water. The alkaline mother liquor and wash water are stored in a hold tank for further use. Transfer the washed EDTN wet cake (90%–95% solids) 576 lbs to a slurry tank where 260 gals water is charged to give a 26% EDTN slurry (stock solution). Saponify as described in (2b) infra.

(2a) Pump the partially cooled slurry directly to the saponification vessel to which is added 96 lbs of caustic soda (dry basis) in addition to the regular caustic charge as well as any alkaline mother liquor and wash water from previous runs in which EDTN was isolated and washed. If these solutions are used, no water should be added to the normal saponification charge.

(2b) Charge 1200 lbs of NaOH to a hydrolysis reactor and add 68 gals water. Heat the contents of the reactor to about 100° C. Add 5,970 lbs of EDTN slurry from the slurry tank, to the hydrolysis reactor. Once saponification is initiated, the rate of slurry addition will be limited by tank freeboard and the capacity of the ammonia absorption system.

Hold the reactor at boil for an additional hour to boil off ammonia. (The aqueous ammonia vapors are vented to an ammonia scrubber.)

Slowly charge small amounts of HCHO to the hydrolysis reactor. The concentration of cyanide ion is monitored and the HCHO feed is stopped when the cyanide ion concentration in the reactor is less than 10 ppm.

Cool the reactor contents from 100° to 80° C. and slowly charge small quantities of $H_2O_2$ while the APHA color is monitored. The $H_2O_2$ feed is discontinued when the color is less than 375.

The product concentration is determined and demineralized water is added to give a solution concentration of 30% calculated as EDTA acid.

EDTA tetrasodium salt bulk solution (30% as EDTA) is the product. (Yield based on EDA=98+%).

What is claimed is:

1. In the formation of ethylenediamine tetraacetonitrile from ethylenediamine, formaldehyde and hydrocyanic acid, the process improvement which comprises
   (1) allowing the adduct formed from ethylene diamine and two molar equivalent amounts of formaldehyde to react with about two molar equivalent amounts of hydrocyanic acid at a temperature no greater than about 30° C. and at an alkaline pH of from about 8 to 10 so as to form a solution of ethylenediamine diacetonitrile in the reaction mixture; and (2) thereafter, as a discrete step, adding said ethylenediamine diacetonitrile solution to at least two molar equivalent amounts of hydrocyanic acid and at least two molar equivalent amounts of formaldehyde at an acidic pH at or below 1.0 so as to form said ethylenediamine tetraacetonitrile as a solid precipitate, said formation of ethylenediamine tetraacetonitrile being conducted below a temperature about 70° C. by the addition of an inert coolant or cooled mother liquor separated from precipitated ethylenediamine tetraacetonitrile to the reaction mixture.

2. The process according to claim 1 wherein the coolant comprises a portion of the mother liquor which has been separated from the precipitated ethylenediamine tetraacetonitrile, which portion has been cooled to from 20° to 30° C. and recycled.

3. The process according to claim 2 wherein said hydrocyanic acid is added to said adduct of ethylenediamine and formaldehyde at such rates that the temperature is maintained at no greater than about 30° C.

4. The process according to claim 3 wherein prior to said reaction with hydrocyanic acid, said adduct is cooled to a degree sufficient to maintain said reaction mixture at temperatures at or below about 30° C.

5. The process according to claim 2 wherein said ethylenediamine diacetonitrile is added to a mixture of formaldehyde and hydrocyanic acid, the pH of which mixture has been previously adjusted to at or below about 1.0 through the addition of acid.

6. The process according to claim 5 wherein said mixture of formaldehyde and hydrocyanic acid is cooled to below about 30° C. prior to said addition of ethylenediamine diacetonitrile.

7. The process according to claim 5 wherein said formaldehyde and hydrocyanic acid are present in an amount corresponding to about 10% excess over the stoichiometric amount for the quantity of ethylenediamine diacetonitrile to be added.

* * * * *